United States Patent
Kleemann

(10) Patent No.: US 6,878,748 B2
(45) Date of Patent: Apr. 12, 2005

(54) FLUORINATED CYCLOALKYL-DERIVATIZED BENZOYLGUANIDINES, PROCESS FOR THEIR PREPARATION, THEIR USES AS MEDICAMENT, AND MEDICAMENT CONTAINING THEM

(75) Inventor: Heinz-Werner Kleemann, Bischofsheim (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 30 days.

(21) Appl. No.: 10/452,556

(22) Filed: Jun. 2, 2003

(65) Prior Publication Data

US 2004/0048930 A1 Mar. 11, 2004

Related U.S. Application Data

(60) Provisional application No. 60/418,409, filed on Oct. 15, 2002.

(30) Foreign Application Priority Data

Jun. 13, 2002 (DE) .......................................... 102 26 462

(51) Int. Cl.[7] .................... A61K 31/155; C07C 277/10; C07C 277/20
(52) U.S. Cl. ...................................... 514/634; 564/235
(58) Field of Search ........................... 564/235; 514/634

(56) References Cited

U.S. PATENT DOCUMENTS

| | | | |
|---|---|---|---|
| 5,571,842 A | * 11/1996 | Kleemann et al. | .......... 514/618 |
| 5,665,739 A | 9/1997 | Lang | |
| 5,866,610 A | 2/1999 | Lang | |
| 6,057,322 A | 5/2000 | Kleemann | |
| 6,114,393 A | 9/2000 | Lang | |
| 6,348,476 B1 | 2/2002 | Scholz | |
| 6,420,430 B1 | 7/2002 | Linz et al. | |
| 6,462,024 B1 | 10/2002 | Lang | |

OTHER PUBLICATIONS

Baumgarth et al, (2,Methyl-5-(methylsulfonyl)benzoyl)guanidine Na+/H+ Antiporter Inhibitors, J. Medicinal Chemistry; vol. 40; No. 13, 1997; pp. 2017–2034.

Umweltgerechta Olfiltersysteme ersetzen Anschraub–Wechselfilter—Environmental Oil Filter Systems Replace Spin–On–Filters, MTZ Motortechnische Zeitschrift; vol. 55; No. 1; 1994; p. 24.

Konig W. et al., Perchloric Acid In Peptide Chemistry, Peptides, (1990), Proc. European Peptide Symp., 21st (1991), pp. 143–145.

March J. Aliphatic Nucleophillic Subtitution, Advanced Organic Chemistry, 3rd Edition (John Wiley & Sons), 1984, pp 350.

Staab H A, New Methods of Preparative Organic Chemistry IV. Syntheses Using Heterocyclic Amides (Axolides) [*], Angew. Chem. Internat. Edit., vol. 1, No. 7, 1962, pp 351–367.

* cited by examiner

Primary Examiner—Brian Davis
(74) Attorney, Agent, or Firm—Joseph D. Rossi

(57) ABSTRACT

Fluorinated cycloalkyl-derivatized benzoylguanidines of formula I

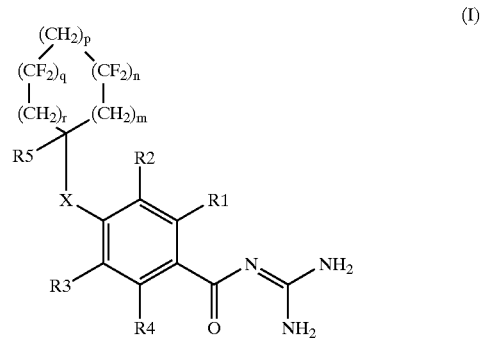

are suitable as antiarrhythmic medicaments with a cardioprotective component for infarction prophylaxis and infarction treatment and for the treatment of angina pectoris.

They also preventively inhibit the pathophysiological processes associated with the development of ischemia-induced damage, in particular in the triggering of ischemia-induced cardiac arrhythmias and of heart failure.

19 Claims, No Drawings

FLUORINATED CYCLOALKYL-DERIVATIZED BENZOYLGUANIDINES, PROCESS FOR THEIR PREPARATION, THEIR USES AS MEDICAMENT, AND MEDICAMENT CONTAINING THEM

CROSS-REFERENCE

This application claims priority from German Application No. 10226462.7, filed Jun. 13, 2002 as well as benefit from U.S. Provisional Application No. 60/418,409, filed Oct. 15, 2002.

Fluorinated cycloalkyl-derivatized benzoylguanidines, process for their preparation, their use as medicament, and medicament containing them.

SUMMARY OF THE INVENTION

The invention relates to compounds of the formula I

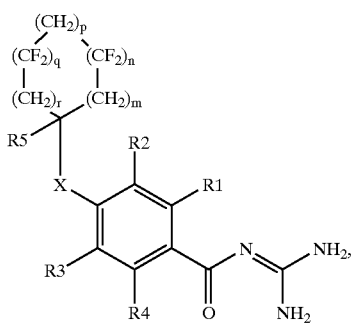

in which:
X is oxygen, sulfur or NR6; wherein
  R6 is hydrogen, alkyl having 1, 2, 3 or 4 carbon atoms or $(CH_2)_k$—$CF_3$, wherein
    k is 0,1, 2 or 3;
m is zero, 1, 2 or 3;
n is zero, 1, 2 or 3;
p is zero, 1, 2, or 3;
q is 1, 2 or 3;
r is zero, 1, 2 or 3;
the total of m, n, p, q and r is 2–8;
R1 is hydrogen, alkyl having 1, 2, 3 or 4 carbon atoms, F, Cl, —OR(7), —NR(8)R(9) or —$C_sF_{2s+1}$, wherein
  R(7), R(8) and R(9) are each, independently of one another, hydrogen, alkyl having 1, 2 or 3 carbon atoms or$(CH_2)$ t—$CF_3$;
s is 1, 2, 3 or 4;
t is 0, 1, 2, 3 or 4;
R2 is hydrogen, F, Cl, alkyl having 1, 2, 3 or 4 carbon atoms or $CF_3$;
R3 is hydrogen, F, Cl, alkyl having 1, 2, 3 or 4 carbon atoms, $CF_3$ or $SO_uR10$;
u is zero, 1 or 2;
R10 is alkyl having 1, 2, 3 or 4 carbon atoms or NR11R12;
R11 and R12 are each, independently of one another, hydrogen or alkyl having 1, 2, 3 or 4 carbon atoms;
R4 is hydrogen, alkyl having 1, 2, 3 or 4 carbon atoms, F, Cl, —OR(13), —NR(14)R(15) or —$C_vF_{2v+1}$;
R(13), R(14) and R(15) are each, independently of one another, hydrogen, alkyl having 1, 2 or 3 carbon atoms or $(CH_2)_w$—$CF_3$;
v is 1,2,3 or 4;
w is 0,1,2,3, or 4;
R5 is hydrogen or F;
and the pharmacologically acceptable salts thereof.

Very particular preference is given to the following compounds of formula I, selected from the group consisting of:
N-[4-(3,3-difluoro-cyclobutoxy)-5-methansulfonyl-2-methyl-benzoyl]-guanidine,
N-[4-(3,3-difluoro-cyclobutylamino)-5-methansulfonyl-2-methyl-benzoyl]-guanidine,
N-{4-[(3,3-difluoro-cyclobutyl)-methyl-amino]-5-methansulfonyl-2-methyl-benzoyl}-guanidine and
N-{4-[(3,3-difluoro-cyclobutyl)-methyl-amino]-5-ethansulfonyl-2-methyl-benzoyl}-guanidine
and their pharmaceutically acceptable salts.

The invention additionally relates to a process for preparing a compound of the formula I, which comprises reacting a compound of the formula II

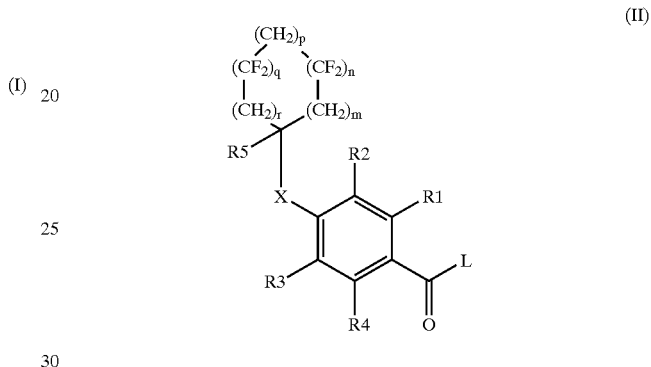

in which R(1) to R(5) and m to r are as defined in formula (I), and L is a leaving group which can easily undergo nucleophilic substitution, with guanidine.

The compounds of formula I are substituted acylguanidines that inhibit the cellular sodium-proton antiporter ($Na^+$/H+-exchanger, NHE).

The compounds of the invention, of formula I , are distinguished by displaying unexpectedly favorable ADME (absorption distribution metabolism excretion) properties compared with known benzoylguanidines, together with excellent inhibition of $Na^+$/$H^+$ exchange; these advantageous properties are dependent on the fluorinated cycloalkyl group.

In contrast to known acylguanidines, the compounds described herein show no unwanted (and disadvantageous) saluretic properties.

Because of their NHE-inhibitory properties, the compounds of formulas I and/or II and/or the pharmaceutically acceptable salts thereof are suitable for the prevention and treatment of diseases caused by activation of or activated NHE, and of diseases caused secondarily by the NHE-related damage.

DETAILED DESCRIPTION

Preferred are compounds of formula I in which:
X is oxygen, sulfur or NR6, wherein
  R6 is hydrogen, methyl or $CH_2$—$CF_3$;
m is zero, 1 or 2;
n is zero, 1 or 2;
p is zero, 1 or 2;
q is 1 or 2;
r is zero, 1 or 2;
the total of m, n, p, q and r is 2–8;
R1 is hydrogen, methyl, F, Cl, —OR(7), —NR(8)R(9) or —$CF_3$;
R(7), R(8) and R(9) are each, independently of one another, hydrogen, methyl, $CF_3$ or $CH_2$—$CF_3$;

R2 is hydrogen, F, Cl, methyl or $CF_3$;
  is hydrogen, F, Cl, alkyl having 1, 2, 3 or 4 carbon atoms, $CF_3$, $SO_2CH_3$ or $SO_2NH_2$;
R4 is hydrogen, methyl, F, Cl, —OR(13), —NR(14)R(15) or —$CF_3$;
R(13), R(14) and R(15) are each, independently of one another, hydrogen, methyl, $CF_3$ or $CH_2$—$CF_3$;
R5 is hydrogen or F;
and the pharmacologically acceptable salts thereof.

Particularly preferred are compounds of formula I in which:
X is oxygen, sulfur or NR6, wherein
  R6 is hydrogen, methyl or $CH_2$—$CF_3$;
m is zero or 1;
n is zero, 1 or 2;
p is zero or 1;
q is 1 or 2;
r is zero or 1;
the total of m, n, p, q and r is 2–8;
R1 is hydrogen, methyl, F, Cl, —OR(7), —NR(8)R(9) or —$CF_3$, wherein
  R(7) is methyl, $CF_3$ or $CH_2$—$CF_3$; and
  R(8) and R(9) are each,
independently of one another, hydrogen, methyl or $CH_2$—$CF_3$;
R2 is hydrogen, F or Cl;
R3 is $CF_3$, $SO_2CH_3$ or $SO_2NH_2$;
R4 is hydrogen;
R5 is hydrogen or F;
and the pharmacologically acceptable salts thereof.

In the compounds of formula I, the substituents R1 to R4, for example, may contain one or more centers of asymmetry. They may thus be, independently of one another, of the S or R configuration. Such compounds may exist as optical isomers, as diasteriomers, as racemates or as mixtures thereof.

The present invention encompasses all tautomeric forms of the compounds of formulas I and II.

In the compounds of the invention, the alkyl radicals may be straight-chain or branched. This also applies if they have substituents or occur as substituents of other radicals, for example in fluoroalkyl radicals or alkoxy radicals. Examples of alkyl radicals are methyl, ethyl, n-propyl, isopropyl (=1-methylethyl), n-butyl, isobutyl (=2-methylpropyl), sec-butyl (=1-methylpropyl) and tert-butyl (=1,1-dimethylethyl). Preferred alkyl radicals are methyl, ethyl, n-propyl and isopropyl. One or more, for example 1, 2, 3, 4 or 5, hydrogen atoms in alkyl radicals may be replaced by fluorine atoms. Examples of such fluoroalkyl radicals are trifluoromethyl, 2,2,2-trifluoroethyl and pentafluoroethyl. Substituted alkyl radicals may be substituted in any positions.

Preferably, in the compounds of formula I, the total of m, n, o, p, q and r is from 2 to 6.

The activated acid derivatives of formula II in which L is an alkoxy, preferably a methoxy, group, a phenoxy group, phenylthio, methylthio, 2-pyridylthio, or a nitrogen heterocycle, preferably 1-imidazolyl, are advantageously obtained in a manner known to the skilled worker from the underlying carbonyl chlorides (formula II, L=Cl), which, in turn, can themselves be prepared in a manner known to the skilled worker from the underlying carboxylic acids (formula II; L=OH), for example, using thionyl chloride.

Beside the carbonyl chlorides of formula II (L=Cl), it is also possible to prepare other activated acid derivatives of formula II in a manner known per se directly from the underlying benzoic acids (formula II; L=OH), such as the methyl esters of formula II with L=$OCH_3$, by treatment with gaseous HCl in methanol; the imidazolides of formula II by treatment with carbonyldiimidazole (L=1-imidazolyl, Staab, Angew. Chem. Int. Ed. Engl. 1, 351–367 (1962)); the mixed anhydrides with Cl—$COOC_2H_5$ or tosyl chloride in the presence of triethylamine in an inert solvent, as activations of benzoic acids with dicyclohexylcarbodiimide (DCC) or with O-[(cyano(ethoxycarbonyl)methylene)amino]-1,1,3,3-tetramethyluronium tetrafluoroborate ("TOTU") (Proceedings of the 21. European Peptide Symposium, Peptides 1990, Editors E. Giralt and D. Andreu, Escom, Leiden, 1991) are possible. A number of suitable methods for preparing activated carboxylic acid derivatives of formula II are indicated in J. March, Advanced Organic Chemistry, third edition (John Wiley & Sons, 1985), page 350, indicating source literature.

Reaction of an activated carboxylic acid derivative of formula II with guanidine takes place in a manner known to the skilled worker in a protic or aprotic polar but inert organic solvent. Those which have proved suitable for the reaction of the methyl benzoates (II; L=$OCH_3$) with guanidine are methanol, isopropanol and THF at temperatures from 20° C. to the boiling point of these solvents. Most reactions of compounds II with salt-free guanidine have advantageously been carried out in aprotic inert solvents, such as THF, dimethoxyethane, dioxane and DMF. However, it is also possible to use water in the presence of a base such as, for example, NaOH as solvent in the reaction of II with guanidine.

If L is Cl, it is advantageous to add an acid scavenger, for example in the form of excess guanidine, to bind the hydrohalic acid.

The carboxylic acid derivatives of formula II can be prepared from compounds of formula III. The underlying benzoic acid derivatives of formula III can be prepared by methods described in the literature.

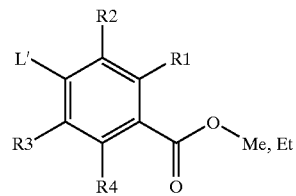

(III)

The introduction of the fluorocycloalkyl nucleophiles into the 4 position takes place by nucleophilic aromatic substitution. Suitably protected benzoic acid derivatives of formula III, such as, for example, the methyl or ethyl esters, are employed in this case. L∝ is a leaving group which can easily be replaced by nucleophilic aromatic substitution, such as F, Cl, Br, I or O—$SO_2CF_3$.

The benzoic acid derivatives of formula II thus obtained are then reacted by one of the process variants described above to give compounds of formula I of the invention.

Benzoylguanidines of formula I are generally weak bases and are able to bind acid to form salts. Suitable acid addition salts are salts of all pharmacologically acceptable acids, for example halides, in particular, hydrochlorides, lactates, sulfates, citrates, tartrates, acetates, phosphates, methylsulfonates, p-toluenesulfonates, etc. Since NHE inhibitors predominantly act via their effect on cellular pH regulation, they can generally be combined beneficially with other compounds which regulate the intracellular pH, with suitable combination partners being inhibitors of the carbonate dehydratase enzyme group, inhibitors of systems transporting bicarbonate ions, such as of the sodium bicarbonate cotransporter (NBC) or of the sodium-dependent chloride-bicarbonate exchanger (NCBE), and NHE inhibitors with inhibitory effect on other NHE subtypes, because it is possible through them to enhance or modulate the pharmacologically relevant pH-regulating effects of the NHE inhibitors described herein.

The use of the compounds of the invention relates to the prevention and treatment of acute and chronic diseases in veterinary and human medicine.

Thus, the NHE inhibitors of the invention are suitable for the treatment of diseases caused by ischemia and by reperfusion.

The compounds described herein are suitable because of their pharmacological properties as antiarrhythmic medicaments.

Owing to their cardioprotective component, the NHE inhibitors of the formula I and/or the pharmaceutically acceptable salts thereof are outstandingly suitable for infarction prophylaxis and infarction treatment and for the treatment of angina pectoris, in which cases they also preventively inhibit or greatly reduce the pathophysiological processes associated with the development of ischemia-induced damage, in particular in the triggering of ischemia-induced cardiac arrhythmias. Because of their protective effects against pathological hypoxic and ischemic situations, the compounds of formula I and/or the pharmaceutically acceptable salts thereof used according to the invention can, because of inhibition of the cellular $Na^+/H^+$ exchange mechanism, be used as medicaments for the treatment of all acute or chronic ischemia-induced damage or diseases induced primarily or secondarily thereby.

This invention also relates to their use as medicaments for surgical interventions. Thus, the compounds can be used during organ transplantations, it being possible to use the compounds both to protect the organs in the donor before and during the removal, to protect removed organs, for example during treatment with or storage thereof in physiological bath liquids, and during transference to the recipient organism.

The compounds of the invention are likewise valuable medicaments with a protective effect when performing angioplastic surgical interventions, for example on the heart as well as on peripheral organs and vessels.

In addition, the compounds of the invention are exceptionally effective medicaments for life-threatening arrhythmias. Ventricular fibrillation is terminated and the physiological sinus rhythm of the heart is restored by their use.

Since NHE1 inhibitors of human tissue and organs, especially the heart, protect effectively not only against damage caused by ischemia and reperfusion but also against the cytotoxic effect of medicaments like those used in particular in cancer therapy and the therapy of autoimmune diseases, combined administration with compounds of formula I and/or the pharmaceutically acceptable salts thereof is suitable for inhibiting the cytotoxic, especially cardiotoxic, side effects of said compounds. The reduction in the cytotoxic effects, especially the cardiotoxicity, resulting from comedication with NHE1 inhibitors makes it additionally possible to increase the dose of the cytotoxic therapeutic agents and/or to prolong the medication with such medicaments. The therapeutic benefits of such a cytotoxic therapy can be considerably increased by combination with NHE inhibitors.

In addition, the NHE1 inhibitors of the invention of formula I and/or the pharmaceutically acceptable salts thereof can be used when there is heart-damaging overproduction of thyroid hormones, thyrotoxicosis, or upon external supply of thyroid hormones. The compounds of formula I and/or the pharmaceutically acceptable salts thereof are thus suitable for improving therapy with cardiotoxic medicaments.

In accordance with their protective effect against ischemia-induced damage, the compounds of the invention are also suitable as medicaments for the treatment of ischemias of the nervous system, especially of the central nervous system, being suitable, for example, for the treatment of stroke or of cerebral edema.

The compounds of formula I and/or II and/or the pharmaceutically acceptable salts thereof are also suitable for the therapy and prophylaxis of diseases and disorders induced by overexcitability of the central nervous system, in particular for the treatment of epileptic disorders, centrally induced clonic and tonic spasms, states of psychological depression, anxiety disorders and psychoses. In these cases it is possible to use the NHE inhibitors described herein alone or in combination with other substances with antiepileptic activity or antipsychotic active ingredients, or carbonate dehydratase inhibitors, for example, with acetazolamide, and with other inhibitors of NHE or of the sodium-dependent chloride-bicarbonate exchanger (NCBE).

The compounds according to the invention, of formula I, and/or the pharmaceutically acceptable salts thereof are additionally likewise suitable for the treatment of types of shock such as, for example, of allergic, cardiogenic, hypovolemic and bacterial shock.

The compounds of formula I and/or the pharmaceutically acceptable salts thereof can likewise be used for the prevention and treatment of thrombotic disorders because they, as NHE inhibitors, are able to inhibit platelet aggregation themselves. They are additionally able to inhibit or prevent the excessive release, occurring after ischemia and reperfusion, of mediators of inflammation and coagulation, especially of von Willebrand factor and of thrombogenic selectin proteins. It is thus possible to use them to reduce and eliminate the pathogenic effect of significant thrombogenic factors. The NHE inhibitors of the present invention can therefore be combined with other anticoagulant and/or thrombolytic active ingredients such as, for example, recombinant or natural tissue plasminogen activator, streptokinase, urokinase, acetylsalicylic acid, thrombin antagonists, factor Xa antagonists, medicinal substances with fibrinolytic activity, thromboxane receptor antagonists, phosphodiesterase inhibitors, factor VIIa antagonists, clopidogrel, ticlopidine etc. Combined use of the present NHE inhibitors with NCBE inhibitors and/or with inhibitors of carbonate dehydratase such as, for example, with acetazolamide, is particularly beneficial.

The compounds of formula I and/or the pharmaceutically acceptable salts thereof according to the invention are additionally distinguished by a strong inhibitory effect on the proliferation of cells, for example fibroblast proliferation and the proliferation of smooth vascular muscle cells. The compounds of formula I and/or the pharmaceutically acceptable salts thereof are therefore suitable as valuable therapeutic agents for diseases in which cellular proliferation represents a primary or secondary cause, and can therefore be used as antiatherosclerotics, agents for chronic renal failure, and for treating cancers.

It is possible to show that cell migration is inhibited by the compounds of the invention. The compounds of the formula I and/or the pharmaceutically acceptable salts thereof are therefore suitable as valuable therapeutic agents for diseases in which cell migration represents a primary or secondary cause, such as, for example, cancers with a pronounced tendency to metastasis.

The compounds of formula I and/or the pharmaceutically acceptable salts thereof are further distinguished by a retardation or prevention of fibrotic disorders. They are thus suitable as agents for the treatment of cardiac fibroses, and of pulmonary fibrosis, hepatic fibrosis, renal fibrosis and other fibrotic disorders.

They can thus be used for the treatment of organ hypertrophies and hyperplasias, for example of the heart and the prostate. They are therefore suitable for the prevention and treatment of heart failure (congestive heart failure=CHF) and for the treatment and prevention of prostate hyperplasia or prostate hypertrophy.

Since there is significant elevation in NHE in essential hypertensives, the compounds of formula I and/or the pharmaceutically acceptable salts thereof are suitable for the prevention and treatment of high blood pressure and of cardiovascular disorders. In these cases, they can be used alone or with a suitable combination and formulation partner for the treatment of high blood pressure and of cardiovascular disorders. Thus, for example, they can be combined with one or more diuretics with a thiazide-like action, loop diuretics, aldosterone and pseudoaldosterone antagonists, such as hydrochlorothiazide, indapamide, polythiazide, furosemide, piretanide, torasemide, bumetanide, amiloride, triamterene, spironolactone or eplerone. The NHE inhibitors of the present invention can further be used in combination with calcium channel blockers, such as verapamil, diltiazem, amlodipine or nifedipine, and with ACE inhibitors, such as, for example, ramipril, enalapril, lisinopril, fosinopril or captopril. Further beneficial combination partners are also beta-blockers, such as metoprolol, albuterol etc., antagonists of the angiotensin receptor and its receptor subtypes such as losartan, irbesartan, valsartan, omapatrilat, gemopatrilat, endothelin antagonists, renin inhibitors, adenosine receptor agonists, inhibitors and activators of potassium channels such as glibenclamide, glimepiride, diazoxide, cromakalim, minoxidil and derivatives thereof, activators of the mitochondrial ATP-sensitive potassium channel (mitoK(ATP) channel), inhibitors of Kv1.5, etc.

NHE1 inhibitors of formula I and/or the pharmaceutically acceptable salts thereof have a significant antiinflammatory effect and can thus be used as antiinflammatory drugs. Inhibition of the release of mediators of inflammation is noteworthy in this connection. The compounds can thus be used alone or in combination with an antiinflammatory drug for the prevention or treatment of chronic and acute inflammatory disorders. Combination partners advantageously used are steroidal and non-steroidal antiinflammatory drugs. The compounds of the invention can also be used for the treatment of disorders caused by protozoa, of malaria and of coccidiosis in poultry.

It has additionally been found that compounds of formula I and/or the pharmaceutically acceptable salts thereof show a beneficial effect on serum lipoproteins. It is generally acknowledged that blood fat levels which are too high, called hyperlipoproteinemias, represent an essential risk factor for the development of arteriosclerotic vascular lesions, especially coronary heart disease. The reduction of elevated serum lipoproteins therefore has exceptional importance for the prophylaxis and regression of atherosclerotic lesions. Beside the reduction in total serum cholesterol, it is particularly important to reduce the proportion of specific atherogenic lipid fractions of this total cholesterol, in particular of the low density lipoproteins (LDL) and of the very low density lipoproteins (VLDL), because these lipid fractions represent an atherogenic risk factor. By contrast, a protective function against coronary heart disease is ascribed to the high-density lipoproteins. Accordingly, hypolipidemics should be able to reduce not only total cholesterol but, in particular, the VLDL and LDL serum cholesterol fractions. It has now been found that NHE1 inhibitors show valuable therapeutically utilizable properties in relation to influencing the serum lipid levels. Thus, they significantly reduce the elevated serum concentrations of LDL and VLDL as are to be observed, for example, due to increased dietary intake of a cholesterol- and lipid-rich diet or in cases of pathological metabolic alterations, for example genetically related hyperlipidemias. They can therefore be used for the prophylaxis and regression of atherosclerotic lesions by eliminating a causal risk factor. Included herein are not only the primary hyperlipidemias but also certain secondary hyperlipidemias occurring, for example, in association with diabetes. In addition, the compounds of formula I and/or the pharmaceutically acceptable salts thereof lead to a marked reduction in the infarctions induced by metabolic abnormalities and, in particular, to a significant reduction in the induced infarct size and the severity thereof.

The compounds of the invention are therefore advantageously used for producing a medicament for the treatment of hypercholesterolemia; for producing a medicament for the prevention of atherogenesis; for producing a medicament for the prevention and treatment of atherosclerosis, for producing a medicament for the prevention and treatment of diseases induced by elevated cholesterol levels, for producing a medicament for the prevention and treatment of diseases induced by endothelial dysfunction, for producing a medicament for the prevention and treatment of atherosclerosis-induced hypertension, for producing a medicament for the prevention and treatment of atherosclerosis-induced thromboses, for producing a medicament for the prevention and treatment of hypercholesterolemia-induced and endothelial dysfunction-induced ischemic damage and post-ischemic reperfusion damage, for producing a medicament for the prevention and treatment of hypercholesterolemia-induced and endothelial dysfunction-induced cardiac hypertrophies and cardiomyopathies and of congestive heart failure (CHF), for producing a medicament for the prevention and treatment of hypercholesterolemia-induced and endothelial dysfunction-induced coronary vasospasms and myocardial infarctions, for producing a medicament for the treatment of said disorders in combinations with hypotensive substances, preferably with angiotensin converting enzyme (ACE) inhibitors and angiotensin receptor antagonists. A combination of an NHE inhibitor of formula I and/or the pharmaceutically acceptable salts thereof with an active ingredient for lowering the blood fat levels, preferably with an HMG-CoA reductase inhibitor (for example lovastatin or pravastatin), the latter bringing about a hypolipidemic effect and thus increasing the hypolipidemic properties of the NHE inhibitor of formula I and/or the pharmaceutically acceptable salts thereof, is a favorable combination with enhanced effect and reduced use of active ingredients.

Thus, compounds of formula I and/or the pharmaceutically acceptable salts thereof contribute to effective protection against endothelial damage of various origins. This protection of the vessels against the syndrome of endothelial dysfunction means that the compounds of formula I and/or the pharmaceutically acceptable salts thereof are valuable medicaments for the prevention and treatment of coronary vasospasms, peripheral vascular diseases, in particular of intermittent claudication, atherogenesis and atherosclerosis, left ventricular hypertrophy and dilated cardiomyopathy and thrombotic disorders.

It has additionally been found that benzoylguanidines of formula I and/or the pharmaceutically acceptable salts thereof are suitable in the treatment of non-insulin-dependent diabetes (NIDDM), in which case insulin resistance is repressed. It is believed that it would be beneficial, to enhance antidiabetic activity, for the compounds of the invention to be combined with a biguanide such as metformin, with an antidiabetic sulfonylurea such as glyburide, glimepiride, tolbutamide etc., with a glucosidase inhibitor, with a PPAR agonist such as rosiglitazone, pioglitazone etc., with an insulin product in a different administration form, with a DB4 inhibitor, with an insulin sensitizer or with meglitinide.

Besides the acute antidiabetic effects, the compounds of formula I and/or the pharmaceutically acceptable salts thereof counteract the development of late complications of diabetes and can therefore be used as medicaments for the prevention and treatment of late damage from diabetes such as diabetic nephropathy, diabetic neuropathy, diabetic retinopathy, diabetic cardiomyopathy and other disorders arising as a result of diabetes. In this connection, they can be combined advantageously with the antidiabetic medicaments described under NIDDM treatment. Combination with a favorable dosage form of insulin could be particularly important.

The NHE inhibitors of the invention, of formula I, and/or the pharmaceutically acceptable salts thereof show, besides the protective effects against acute ischemic events and the subsequent reperfusion events which are equally acutely stressing, also direct therapeutically utilizable effects on disorders and impairments of the entire mammalian organism which are connected with manifestations of the chronically progressing aging process and which are independent of acute hypoperfusion states and occur under normal, nonischemic conditions. These pathological age-related manifestations induced over the long term of aging, which can now be treated with NHE inhibitors, comprise disorders and impairments which are crucially caused by age-related changes in vital organs and their function, and become increasingly important in the aging organism.

Examples of disorders connected with an age-related functional impairment, with age-related signs of wear of organs, include inadequate responsiveness and reactivity of the blood vessels in relation to contraction and relaxation reactions. This age-related decline in vascular reactivity to constricting and relaxing stimuli, which are an essential process in the cardiovascular system and thus of life and health, can be significantly diminished or abolished by NHE inhibitors. An important function and a measure of the maintenance of vascular reactivity is the blocking or slowing of the age-related progression of endothelial dysfunction, which can be abolished highly significantly by NHE inhibitors. The compounds of formula I and/or the pharmaceutically acceptable salts thereof are thus outstandingly suitable for the treatment and prevention of age-related progression of endothelial dysfunction, especially of intermittent claudication.

An example of another variable characterizing the aging process is the decrease in the contractility of the heart and the decrease in the adaptation of the heart to a required pumping performance of the heart. This reduced efficiency of the heart resulting from the aging process is in most cases associated with a dysfunction of the heart, which is caused, inter alia, by deposition of connective tissue in the cardiac tissue. This deposition of connective tissue is characterized by an increase in the weight of the heart, by an enlargement of the heart and by restricted function of the heart. It was surprisingly found that it was possible virtually completely to inhibit such an aging of the heart. The compounds of formula I and/or the pharmaceutically acceptable salts thereof are thus outstandingly suitable for the treatment and prevention of heart failure, particularly of congestive heart failure (CHF). Whereas previous patents and patent applications have claimed the treatment of various types of cancers which have already occurred, it was now extremely surprising that not only the cancer which has already occurred can be cured by inhibition of proliferation, but that the age-related frequency of the development of cancer can be reduced and highly significantly delayed by NHE inhibitors. A particularly noteworthy finding is that disorders occurring in an age-related manner in all organs, and not just certain types of cancer, are suppressed or occur with a highly significant delay. The compounds of formula I and/or the pharmaceutically acceptable salts thereof are thus outstandingly suitable for the treatment and, in particular, the prevention of age-related types of cancer.

There is now found to be not only a delay, shifted highly significantly in time and exceeding the statistically normal extent, in the occurrence of age-related disorders of all investigated organs including the heart, vessels, liver etc., and a highly significant delay in age-related cancer. On the contrary, there is also, surprisingly, a prolongation of life to an extent which has not to date been achievable by any other group of medicaments or by any natural products. This unique effect of NHE inhibitors also makes it possible, besides use of the active ingredients alone on humans and animals, for these NHE inhibitors to be combined with other active principles, measures, substances and natural products used in gerontology and based on a different mechanism of action. Such classes of active ingredients used in gerontological therapy include, in particular, vitamins and substances with antioxidant activity. Since there is a correlation between caloric loading or food intake and the aging process, combination with dietary measures is possible, for example, combination with appetite suppressants. Consideration may likewise be given to combination with hypotensive medicaments, such as with ACE inhibitors, angiotensin receptor antagonists, diuretics, $Ca^{+2}$ antagonists, etc., or with metabolism-normalizing medicaments such as cholesterol-lowering agents.

The compounds of formula I and/or the pharmaceutically acceptable salts thereof are thus outstandingly suitable for the prevention of age-related tissue changes and for prolonging life while maintaining a high quality of life.

The compounds of the invention are effective inhibitors of the cellular sodium/proton antiporter (Na/H exchanger) which, in numerous disorders (essential hypertension, atherosclerosis, diabetes etc.), is elevated also in cells which are easily amenable to measurements, such as, for example, in erythrocytes, platelets or leukocytes. The compounds according to the invention are therefore suitable as excellent and simple scientific tools, for example in their use as diagnostic aids for the determination and differentiation of particular types of hypertension, but also of atherosclerosis, of diabetes and of late complications of diabetes, of proliferative disorders etc.

Additionally claimed is a medicine for human, veterinary or phytoprotective use comprising an effective amount of one or more compounds of formula I and/or the pharmaceutically acceptable salts thereof, together with pharmaceutically acceptable carriers and additives, alone or in combination with other pharmacological active ingredients or medicaments.

Medicaments comprising a compound of formula I can, moreover, for example, be administered orally, parenterally, intravenously, rectally, percutaneously or by inhalation, with the preferred method of administration being dependent on the particular nature of the disorder. The compounds of formula I can, moreover, be used alone or together with pharmaceutical excipients, both in veterinary medicine and in human medicine. The medicaments generally contain active ingredients of formula I and/or the pharmaceutically acceptable salts thereof in an amount of 0.01 mg to 1 g per dose unit.

Excipients suitable for the desired pharmaceutical formulation are familiar to the skilled worker on the basis of his expert knowledge. In addition to solvents, gel formers, suppository bases, tablet excipients and other carriers for active ingredients, it is possible to use, for example, antioxidants, dispersants, emulsifiers, antifoams, masking flavors, preservatives, solubilizers, colors, etc.

For a form for oral use, the active compounds are mixed with the additives suitable for this purpose, such as carriers, stabilizers or inert diluents, and converted by conventional methods into suitable dosage forms such as tablets, coated tablets, two-piece capsules, aqueous, alcoholic or oily solutions. Examples of inert carriers which can be used are gum arabic, magnesia, magnesium carbonate, potassium phosphate, lactose, glucose and starch, especially corn starch. Preparation can, moreover, take place using both dry and wet granules. Examples of suitable oily carriers or solvents are vegetable or animal oils such as sunflower oil or fish liver oil.

For subcutaneous or intravenous administration, the active compounds are converted into a solution, suspension or emulsion, if desired with the substances customary for this purpose, such as solubilizers, emulsifiers or other excipients. Examples of suitable solvents are: water, physiological saline or alcohols, for example ethanol, propanol, glycerol, as well as sugar solutions such as glucose or mannitol solutions, or else a mixture of the various solvents mentioned.

Suitable as pharmaceutical formulation for administration in the form of aerosols or sprays are, for example, solutions, suspensions or emulsions of the active ingredient of formula I in a pharmaceutically acceptable solvent such as, in particular, ethanol or water, or a mixture of such solvents.

The formulation may, if required, also comprise other pharmaceutical excipients such as surfactants, emulsifiers and stabilizers, and a propellant gas. Such a preparation normally contains the active ingredient in a concentration of about 0.1 to 10, in particular of about 0.3 to 3% by weight.

The dosage of the active ingredient of formula I to be administered and the frequency of administration depend on the potency and duration of action of the compounds used as well as on the nature and severity of the disorder to be treated, and on the sex, age, weight and individual response of the mammal to be treated.

On average, the daily dose of a compound of formula I for a patient weighing about 75 kg is at least 0.001 mg/kg, preferably 0.01 mg/kg, up to a maximum of 10 mg/kg, preferably 1 mg/kg, of bodyweight. For acute episodes of the disorder, for example immediately after suffering a myocardial infarction, it may be necessary for the dosages also to be higher. Especially with i.v. use, for example for an infarct patient in an intensive care unit, up to 700 mg/kg per day may be necessary. The daily dose can be divided into several, for example up to 4, individual doses.

List of Abbreviations:

| | |
|---|---|
| ADME | absorption-distribution-metabolism-excretion |
| CDI | Di-imidazol-1-yl-methanone |
| DIP | diisopropyl ether |
| DMF | N,N-dimethylformamide |
| EA | ethyl acetate (EtOAc) |
| EI | electron impact |
| eq. | equivalent |
| ES | electrospray ionization |
| Et | ethyl |
| HEP | n-heptane |
| KOtBu | potassium 2-methylpropan-2-olate |
| Me | methyl |
| MeOH | methanol |
| mp | melting point |
| MTB | 2-Methoxy-2-methyl-propane |
| NMP | 1-methylpyrrolidin-2-one |
| RT | room temperature |
| THF | tetrahydrofuran |

EXAMPLE 1

N-[4-(3,3-Difluorocyclobutoxy)-5-methanesulfonyl-2-methylbenzoyl]guanidine

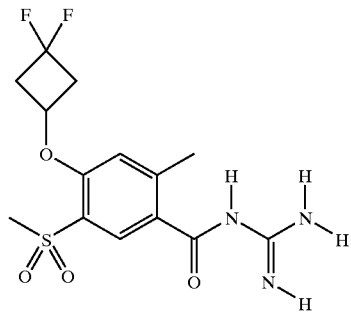

a) (3,3-Difluorocyclobutoxymethyl)benzene 20.0 g of 3-benzyloxycyclobutanone (Bull. Chem. Soc. Jpn. (1984), 57(6), 1637) were dissolved in 150 ml of CH$_2$Cl$_2$, and a solution of 25.0 g of [bis(2-methoxyethyl)amino]sulfur trifluoride in 30 ml of CH$_2$Cl$_2$ was added dropwise at RT (room temperature). After stirring at RT for 5 h, 12.0 g of diethylaminosulfur trifluoride were added. After stirring at RT for a further 20 h, the reaction mixture was washed 3 times with 100 ml of water each time. It was dried over Na$_2$SO$_4$, and the solvent was removed in vacuo. Chromatography on silica gel with EA/HEP 3:1 and subsequent kugelrohr distillation afforded 27.6 g of a colorless oil.

b) 3,3-Difluorocyclobutanol 22.4 g of (3,3-difluorocyclobutoxymethyl)benzene were dissolved in 100 ml of diethyl ether, and 1.4 g of 10% Pd/C were added. Hydrogenation was carried out at RT under 20 bar of H$_2$ for 5 h. The catalyst was washed with 10 ml of diethyl ether, and the solution was distilled. 14.0 g of the product (boiling point 80° C.) were obtained as a mixture with diethyl ether and toluene. This mixture was reacted without further purification.

c) Methyl 4-(3,3-difluorocyclobutoxy)-5-methanesulfonyl-2-methylbenzoate 370 mg of methyl 4-fluoro-5-methanesulfonyl-2-methylbenzoate, 297 mg of 3,3-difluorocyclobutanol and 1.47 g of Cs$_2$CO$_3$ were dissolved in 10 ml of anhydrous NMP and stirred at 60° C. for 4 h. The reaction mixture was then diluted with 125 ml of a 50% concentrated aqueous NaHCO$_3$ solution and extracted 3 times with 100 ml of EA each time. It was dried over Na$_2$SO$_4$, and the solvent was removed in vacuo. Chromatography on silica gel with DIP resulted in 380 mg of a colorless oil.

Rf (DIP)=0.21 MS (DCI): 335 d) N-[4-(3,3-Difluorocyclobutoxy)-5-methanesulfonyl-2-methylbenzoyl]guanidine 566 mg of guanidinium chloride were dissolved in 5 ml of anhydrous DMF and added to a solution of 604 mg of KOtBu in 5 ml of anhydrous DMF. This solution of guanidine in DMF prepared in this way was added to a solution of 360 mg of methyl 4-(3,3-difluorocyclobutoxy)-5-methanesulfonyl-2-methylbenzoate in 5 ml of DMF and stirred at RT for 24 h. The reaction mixture was diluted with 125 ml of a 50% concentrated aqueous NaHCO$_3$ solution and extracted 3 times with 80 ml of EA each time. It was dried over Na$_2$SO$_4$, and the solvent was removed in vacuo. Chromatography on silica gel with EA/MeOH 5:1 afforded 175 mg of colorless crystals, mp 273° C. (with decomposition).

Rf (EA/MeOH 5:1)=0.50 MS (ES$^+$): 362

EXAMPLE 2

N-[4-(3,3-Difluoro-cyclobutylamino)-5-methanesulfonyl-2-methyl-benzoyl]-guanidine

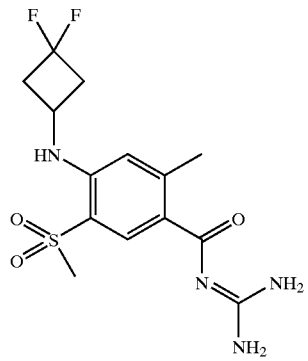

a) 3,3-Difluoro-cyclobutylamine, Hydrochloride 16.7 g 3,3-Difluoro-cyclobutanecarboxylic acid (J. Org. Chem. 1987,52,1872) were dissolved using 180 ml CHCl$_3$ and 36 ml H$_2$SO$_4$ (98%) added. The mixture was warmed up to 50° C. At this temperature, 16 g NaN$_3$ were added in small portions during 45 minutes. Stirring was continued for 2 h, then the mixture was cooled to ambient temperature and poured on 250 g of ice. The mixture was extracted three times using 100 ml of diethylether each time to isolate 0.7 g of unconverted 3,3-difluoro-cyclobutanecarboxylic acid. The pH of the aqueous layer was adjusted to pH=12–13 using an aqueous solution of NaOH and extracted three times using 100 ml of CH$_2$Cl$_2$ each time. The organic layer was washed using 100 ml of water, 130 ml of a 2 N aqueous HCl solution added and, finally, the volatiles were removed in vacuo. Yield: 15.3 g of a colourless solid, mp 315° C. (decomposition).

b) N-(3,3-Difluoro-cyclobutyl)-methansulfonamide 0.60 g 3,3-Difluoro-cyclobutylamine hydrochloride were suspended using 40 ml CH$_2$Cl$_2$ and 2.9 ml of triethylamine added at ambient temperature while receiving a clear solution. Thereafter, 1.0 ml of methanesulfonylchloride were added dropwise at ambient temperature and the mixture left at that temperature for 16 h. The volatiles were removed in vacuo, the residue was redissolved using 200 ml of EE and 100 ml of a saturated aqueous Na$_2$CO$_3$-solution and the layers separated. The organic layer was washed twice using 20 ml of a saturated aqueous NaHSO$_4$-solution each time and washed twice using 30 ml of a saturated aqueous Na$_2$CO$_3$-solution each time. The organic layer was dried over MgSO$_4$ and the solvent removed in vacuo. Yield: 700 mg of a colorless resin.

Rf (EE)=0.28 MS (DCI): 186 c) 4-(3,3-Difluoro-cyclobutylamino)-5-methanesulfonyl-2-methyl-benzoic Acid Methyl Ester 0.70 g of N-(3,3-Difluoro-cyclobutyl)-methanesulfonamide, 0.93 g of 4-fluoro-5-methanesulfonyl-2-methyl-benzoic acid methyl ester, and 1.5 ml of N''-tert-butyl-N,N,N',N'-tetramethyl-guanidine were dissolved using 10 ml NMP (anhydrous) and stirred for 6 h at 150° C. The reaction mixture was cooled to ambient temperature and 200 ml of EE added. This solution was washed three times using 20 ml of a saturated aqueous NaHSO$_4$-solution each time. Thereafter, the organic layer was washed three times using 30 ml of a saturated aqueous Na$_2$CO$_3$-solution each time. The organic layer was dried over MgSO$_4$ and the solvent removed in vacuo. Chromatography on silica gel using DIP yielded 220 mg of a colourless foam.

Rf (DIP)=0.31 MS (ES$^+$):334 d) 4-(3,3-Difluoro-cyclobutylamino)-5-methanesulfonyl-2-methyl-benzoic Acid 210 mg of 4-(3,3-Difluoro-cyclobutylamino)-5-methanesulfonyl-2-methyl-benzoic acid methyl ester were dissolved using 10 ml of dioxane, and 0.47 ml of a 2N aqueous NaOHsolution was added. The mixture was stirred for 18 h at ambient temperature. Afterwards, the solvents were removed in vacuo. The residue was then taken up using 10 ml of water. The pH was adjusted to pH=2 using an aqueous HClsolution and extracted three times using 20 ml of EE each time. The organic layer was dried over MgSO$_4$ and the solvent removed in vacuo. Yield: 196 mg of an amorphous solid.

Rf (EE)=0.40 MS (ES$^-$): 318 e) N-[4-(3,3-Difluoro-cyclobutylamino)-5-methanesulfonyl-2-methyl-benzoyl]-guanidine 40 mg of 4-(3,3-Difluoro-cyclobutylamino)-5-methanesulfonyl-2-methyl-benzoic acid were dissolved using 1 ml of DMF (anhydrous), and 26 mg of CDI were added at ambient temperature. Stirring was continued at ambient temperature for 6 h to yield the intermediate imidazolide. In the meantime, 72 mg of guanidine-hydrochloride and 70 mg of KOtBu were dissolved using 1 ml of DMF (unhydrous) and stirred for 30 minutes at ambient temperature. This solution of guanidine (free base) was then added to the above solution of the imidazolide and left for 18 h at ambient temperature. Thereafter, 50 ml of water were added and the pH adjusted to pH=8 using diluted aqueous HCl solution. The mixture was extracted three times using 10 ml of EE. The organic layer was dried over MgSO$_4$ and the solvent removed in vacuo. Yield: 37 mg of an amorphous solid.

Rf (EE/MeOH 10:1)=0.12 MS (ES$^+$): 360

The NHE-1 inhibition was determined as follows:

FLIPR assay for determining NHE-1 inhibitors by measurement of the recovery in pH$_i$ in transfected cell lines which express human NHE-1

The assay is carried out in an FLIPR (fluorescent imaging plate reader) with black-walled 96-well microtiter plates with clear bases. The transfected cell lines expressing the various NHE subtypes (the parental cell line LAP-1 shows no endogenous NHE activity as a result of mutagenesis and subsequent selection) are seeded the preceding day at a density of ~25 000 cells/well.

(The growth medium for the transfected cells (Iscove +10% fetal calf serum) additionally contains G418 as selection antibiotic in order to ensure the presence of the transfected sequences.)

The actual assay starts with the removal of the growth medium and addition of 100 μl of loading buffer per well (5 μM BCECF-AM [2',7'-bis(carboxyethyl)-5-(and -6)-carboxyfluorescein, acetoxymethyl ester] in 20 mM NH$_4$Cl, 115 mM choline chloride, 1 mM MgCl$_2$, 1 mM CaCl$_2$, 5 mM KCl, 20 mM HEPES, 5 mM glucose; pH 7.4 [adjusted with KOH]). The cells are then incubated at 37° C. for 20 minutes. This incubation leads to loading of the cells with the fluorescent dye whose fluorescence intensity depends on pHi, and with NH$_4$Cl, which makes the cells slightly alkaline. [The nonfluorescent dye precursor BCECF-AM is, -as ester, membrane-permeable. The actual dye BCECF, which is not membrane-permeable, is liberated inside cells by esterases.]

After this incubation for 20 minutes, the loading buffer, which contains NH$_4$Cl and free BCECF-AM, is removed by washing three times in a cell washer (Tecan Columbus) with, in each case, 400 μl of washing buffer (133.8 mM choline chloride, 4.7 mM KCl, 1.25 mM MgCl$_2$, 1.25 mM CaCl$_2$, 0.97 mM K$_2$HPO$_4$, 0.23 mM KH$_2$PO$_4$, 5 mM HEPES, 5 mM glucose; pH 7.4 [adjusted with KOH]). The residual volume remaining in the wells is 90 μl (50–125 μl possible). This washing step removes the free BCECF-AM and results, as a consequence of the removal of the external NH$_4^+$ ions, in intracellular acidification ($\sim$pH$_i$ 6.3–6.4).

Since the equilibrium of intracellular NH$_4^+$ with NH$_3$ and H$^+$ is disturbed by the removal of the extracellular NH$_4^+$ and by the subsequent instantaneous passage of the NH$_3$ through the cell membrane, the washing process results in H$^+$ remaining inside the cells, which is the cause of the intracellular acidification. This may eventually lead to cell death if it persists long enough.

It is important at this point that the washing buffer is sodium-free (<1 mM) because extracellular sodium ions would lead to an instantaneous recovery of the pH$_i$ through the activity of the cloned NHE isoforms.

It is likewise important for all the buffers used (loading buffer, washing buffer, recovery buffer) not to contain any HCO$_3^-$ ions, because the presence of bicarbonate would lead to activation of interfering bicarbonate-dependent pH$_i$ regulatory systems present in the parental LAP-1 cell line.

The microtiter plates with the acidified cells are then (up to 20 minutes after the acidification) transferred to the FLIPR. In the FLIPR, the intracellular fluorescent dye is excited by light with a wavelength of 488 nm generated by an argon laser, and the measured parameters (laser power, illumination time and aperture of the CCD camera incorporated in the FLIPR) are chosen so that the average fluorescence signal per well is between 30,000 and 35,000 relative fluorescence units.

The actual measurement in the FLIPR starts with a photograph being taken by the CCD camera every two seconds under software control. After ten seconds, the recovery of the intracellular pH is initiated by adding 90 μl of recovery buffer (133.8 mM NaCl, 4.7 mM KCl, 1.25 mM MgCl$_2$, 1.25 mM CaCl$_2$, 0.97 mM K$_2$HPO$_4$, 0.23 mM KH$_2$PO$_4$, 10 mM HEPES, 5 mM glucose; pH 7.4 [adjusted with NaOH]) by means of the 96-well pipettor incorporated in the FLIPR.

Positive control wells (100% NHE activity) are those to which pure recovery buffer is added, while negative controls (0% NHE activity) receive washing buffer. Recovery buffer with twice the concentration of test substance is added to all the other wells. Measurement in the FLIPR terminates after 60 measurements (two minutes).

The raw data are exported into the Activity Base program. This program first calculates the NHE activities for each tested substance concentration and, from these, the IC$_{50}$ values for the substances. Since the progress of pH$_i$ recovery is not linear throughout the experiment, but falls at the end owing to decreasing NHE measurement the part in which the increase in fluorescence of the positive controls is linear.

| Example | NHE1 inhibition IC$_{50}$ [nM] |
|---------|-------------------------------|
| 1       | 5.9                           |

I claim:
1. A fluorinated cycloalkyl-derivatized benzoylguanidine of formula I

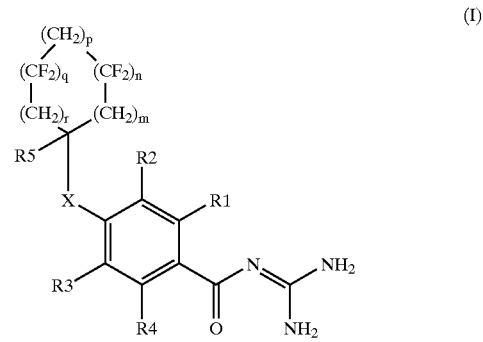

in which:
  X is oxygen, sulfur or NR6; wherein
    R6 is hydrogen, alkyl having 1, 2, 3 or 4 carbon atoms or (CH$_2$)$_k$—CF$_3$;
    k is 0, 1, 2 or 3;
  m is zero, 1, 2 or 3;
  n is zero, 1, 2 or 3;
  p is zero, 1, 2, or 3;
  q is 1,2 or 3;
  r is zero, 1, 2 or 3;
  the total of m, n, p, q and r is 2–8;
  R1 is hydrogen, alkyl having 1, 2, 3 or 4 carbon atoms, F, Cl, —OR(7), —NR(8)R(9) or —C$_s$F$_{2s+1}$, wherein
    R(7), R(8) and R(9) are each, independently of one another, hydrogen, alkyl having 1, 2 or 3 carbon atoms or (CH$_2$)$_t$—CF$_3$;
    s is 1, 2, 3 or 4;
    t is 0, 1, 2, 3 or 4;
  R2 is hydrogen, F, Cl, alkyl having 1, 2, 3 or 4 carbon atoms or CF$_3$;
  R3 is hydrogen, F, Cl, alkyl having 1, 2, 3 or 4 carbon atoms, CF$_3$ or SO$_u$R10;
  u is zero, 1 or 2;
  R10 is alkyl having 1, 2, 3 or 4 carbon atoms or NR11R12;
    R11 and R12 are each, independently of one another, hydrogen or alkyl having 1, 2, 3 or 4 carbon atoms;
  R4 is hydrogen, alkyl having 1, 2, 3 or 4 carbon atoms, F, Cl, —OR(13), —NR(14)R(15) or —C$_v$F$_{2v+1}$;
  R(13), R(14) and R(15) are each, independently of one another, hydrogen, alkyl having 1, 2 or 3 carbon atoms or (CH$_2$)$_w$—CF$_3$;
  v is 1, 2, 3 or 4;
  w is 0, 1, 2, 3, or 4;

R5 is hydrogen or F;
and the pharmacologically acceptable salts thereof.

2. A compound of formula I as claimed in claim 1, wherein
X is oxygen, sulfur or NR6, wherein
R6 is hydrogen, methyl or $CH_2$—$CF_3$;
m is zero, 1 or 2;
n is zero, 1 or 2;
p is zero, 1 or 2;
q is 1 or 2;
r is zero, 1 or 2;
the total of m, n, p, q and r is at least 2;
R1 is hydrogen, methyl, F, Cl, —OR(7), —NR(8)R(9) or —$CF_3$;
R(7), R(8) and R(9) are each,
independently of one another, hydrogen, methyl, $CF_3$ or $CH_2$—$CF_3$;
R2 is hydrogen, F, Cl, methyl or $CF_3$;
R3 is hydrogen, F, Cl, alkyl having 1, 2, 3 or 4 carbon atoms, $CF_3$, $SO_2CH_3$ or $SO_2NH_2$;
R4 is hydrogen, methyl, F, Cl, —OR(13), —NR(14)R(15) or —$CF_3$;
R(13), R(14) and R(15) are each,
independently of one another, hydrogen, methyl, $CF_3$ or $CH_2$—$CF_3$;
R5 is hydrogen or F.

3. A compound of formula I as claimed in claim 1, wherein:
X is oxygen, sulfur or NR6, wherein
R6 is hydrogen, methyl or $CH_2$—$CF_3$;
m is zero or 1;
n is zero, 1 or 2;
p is zero or 1;
q is 1 or 2;
r is zero or 1;
the total of m, n, p, q and r being at least 2;
R1 is hydrogen, methyl, F, Cl, —OR(7), —NR(8)R(9) or —$CF_3$; wherein
R(7) is methyl, $CF_3$ or $CH_2$—$CF_3$; and
R(8) and R(9) are each,
independently of one another, hydrogen, methyl or $CH_2$—$CF_3$;
R2 is hydrogen, F or Cl;
R3 is $CF_3$, $SO_2CH_3$ or $SO_2NH_2$;
R4 is hydrogen;
R5 is hydrogen or F.

4. A compound of claim 1, selected from the group consisting of:
N-[4-(3,3-difluoro-cyclobutoxy)-5-methansulfonyl-2-methyl-benzoyl]-guanidine,
N-[4-(3,3-difluoro-cyclobutylamino)-5-methansulfonyl-2-methyl-benzoyl]-guanidine,
N-{4-[(3,3-difluoro-cyclobutyl)-methyl-amino]-5-methansulfonyl-2-methyl-benzoyl}-guanidine, and
N-{4-[(3,3-difluoro-cyclobutyl)-methyl-amino]-5-ethansulfonyl-2-methyl-benzoyl}-guanidine and their pharmaceutically acceptable salts.

5. A medicament comprising the compound of claim 1.

6. A method for the treatment or prophylaxis of a condition selected from the group consisting of acute or chronic damage, disorders or indirect sequelae of organs and tissues caused by ischemic events or by reperfusion events, arrhythmias, life-threatening ventricular fibrillation of the heart, myocardial infarction, angina pectoris, ischemic states of the heart, ischemic states of the peripheral and central nervous system, stroke, ischemic states of peripheral organs and tissues, states of shock, diseases wherein cell proliferation represents a primary or secondary cause, cancer, metastasis, prostate hypertrophy, prostate hyperplasia, atherosclerosis, impairments of lipid metabolism, high blood pressure, disorders of the central nervous system, anxiety, depression psychoses, non-insulin-dependent diabetes mellitus (NIDDM) thromboses, disorders resulting from endothelial dysfunction, intermittent claudication, fibrotic disorders of internal organs, fibrotic disorders of the liver, fibrotic disorders of the kidney, fibrotic disorders of vessels, fibrotic disorders of the heart, and heart failure, said method comprising administering to a mammal in need thereof an effective amount for the desired treatment of a composition comprising a compound of claim 1.

7. A pharmaceutical composition comprising a compound of formula I as claimed in claim 1 in combination with another medicament or active ingredient for the treatment or prophylaxis of a condition selected from the group consisting of acute or chronic damage, disorders or indirect sequelae of organs and tissues caused by ischemic events or by reperfusion events, arrhythmias, life-threatening ventricular fibrillation of the heart, myocardial infarction, angina pectoris, ischemic states of the heart, ischemic states of the peripheral and central nervous system, stroke, ischemic states of peripheral organs and tissues, states of shock, diseases wherein cell proliferation represents a primary or secondary cause, cancer, metastasis, prostate hypertrophy, prostate hyperplasia, atherosclerosis, impairments of lipid metabolism, high blood pressure, disorders of the central nervous system, anxiety, depression psychoses, non-insulin-dependent diabetes mellitus (NIDDM), thromboses, disorders resulting from endothelial dysfunction, intermittent claudication, fibrotic disorders of internal organs, fibrotic disorders of the liver, fibrotic disorders of the kidney, fibrotic disorders of vessels, fibrotic disorders of the heart, and heart failure.

8. The composition as claimed in claim 7 wherein said other medicament is selected from the group consisting of the cardiotoxic and cytotoxic medicaments and active ingredients, said composition having reduced cardiotoxic and cytotoxic properties.

9. The method of claim 6 for the treatment or prophylaxis of acute and chronic impairments, disorders or indirect subsequent disorders of organs and limbs caused by ischemic events or by reperfusion events.

10. The method of claim 6 for the treatment of life-threatening ventricular fibrillation of the heart.

11. The method of claim 6 for the treatment of or prophylaxis of metastasis.

12. The method of claim 6 for the treatment or prophylaxis of fibrotic heart diseases, of heart failure or of congestive heart failure.

13. A medicine for human, veterinary and/or phytoprotective use comprising at least one compound of claim 1, together with one or more pharmaceutically acceptable carriers and additives.

14. A medicine as claimed in claim 13 further comprising at least one other pharmacological active ingredient or medicament.

15. A method for preserving and restoring transplans for surgical procedures comprising administering to a mammal in need thereof an effective amount for the desired treatment of a composition comprising a compound of claim 1.

16. A method for preventing age-related tissue change comprising administering to a mammal in need thereof an effective amount for the desired treatment of a composition comprising a compound of claim 1.

17. A pharmaceutical composition comprising a compound of formula I as claimed in claim 1 in combination with another medicament or active ingredient for preserving and restoring transplants for surgical procedures.

18. A pharmaceutical composition comprising a compound of formula I as claimed in claim 1 in combination with another medicament or active ingredient for preventing age-related tissue change.

19. A method for prolonging life comprising administering to a mammal in need thereof an effective amount for the desired treatment of a composition comprising a compound of claim 1.

* * * * *